US008920353B2

(12) United States Patent
Hinshon et al.

(10) Patent No.: US 8,920,353 B2
(45) Date of Patent: Dec. 30, 2014

(54) ADJUSTABLE LUMBO-SACRAL ORTHOSIS

(71) Applicant: Orthotic Solutions, LLC, Blaine, MN (US)

(72) Inventors: Patrick Scott Hinshon, Maplewood, MN (US); Thomas E. Kramer, Andover, MN (US)

(73) Assignee: Orthotic Solutions, LLC, Blaine, MN (US)

( * ) Notice: Subject to any disclaimer, the term of this patent is extended or adjusted under 35 U.S.C. 154(b) by 0 days.

(21) Appl. No.: 13/632,880

(22) Filed: Oct. 1, 2012

(65) Prior Publication Data
US 2013/0030338 A1 Jan. 31, 2013

Related U.S. Application Data

(63) Continuation-in-part of application No. 13/472,882, filed on May 16, 2012, now abandoned.

(60) Provisional application No. 61/611,669, filed on Mar. 16, 2012, provisional application No. 61/622,204, filed on Apr. 10, 2012, provisional application No. 61/486,438, filed on May 16, 2011.

(51) Int. Cl.
*A61F 5/00* (2006.01)
(52) U.S. Cl.
USPC ................................. 602/19; 602/5
(58) Field of Classification Search
USPC ....................... 602/17–19; 128/845, 869, 870, 128/874–875; 2/336–338
See application file for complete search history.

(56) References Cited

U.S. PATENT DOCUMENTS

| 3,116,735 | A | | 1/1964 | Geimer |
| 3,717,143 | A | * | 2/1973 | Johnson .......................... 602/19 |
| 3,945,376 | A | | 3/1976 | Kuehnegger |
| 4,475,543 | A | * | 10/1984 | Brooks et al. ................... 602/19 |
| 5,362,304 | A | | 11/1994 | Varn |
| 5,405,313 | A | | 4/1995 | Albin |
| 5,820,575 | A | * | 10/1998 | Cabrera et al. .................. 602/19 |
| 6,063,047 | A | | 5/2000 | Minne |
| 6,099,490 | A | | 8/2000 | Turtzo |
| 6,478,759 | B1 | | 11/2002 | Modglin et al. |
| 6,666,838 | B2 | | 12/2003 | Modglin et al. |
| 6,766,532 | B1 | | 7/2004 | Cabana |
| 6,899,689 | B1 | | 5/2005 | Modglin |
| 6,926,685 | B1 | | 8/2005 | Modglin |

(Continued)

FOREIGN PATENT DOCUMENTS

| DE | 2556086 | 7/1976 |
| EP | 0917864 | 8/2007 |

(Continued)

*Primary Examiner* — Michael Brown
(74) *Attorney, Agent, or Firm* — Thomas J. Oppold; Larkin Hoffman Daly & Lindgren, Ltd.

(57) ABSTRACT

A lumbo-sacral orthosis having a main body member sized to wrap substantially around a body of a wearer at the wearer's lumbar and sacral region. An outer holds the main body member at the wearer's lumbar and sacral region. An inner belt is cinched to compresses the wearer's body at the waist groove. A lumbar panel with an independently movable flexible element may be supported by the main body member. Side panels may also be supported by the main body member along with an abdominal panel which may include an independently movable lower element.

19 Claims, 8 Drawing Sheets

(Inside)

(56) References Cited

U.S. PATENT DOCUMENTS

| | | |
|---|---|---|
| 7,001,348 B2 | 2/2006 | Garth et al. |
| 7,320,670 B1 | 1/2008 | Modglin |
| 7,507,214 B2 | 3/2009 | Smith, Jr. |
| 7,905,849 B2 | 3/2011 | Park |
| 8,012,113 B2 | 9/2011 | Lee et al. |
| 8,226,587 B2 | 7/2012 | Segal et al. |
| D666,301 S | 8/2012 | Joseph |
| 8,235,925 B2 | 8/2012 | Cavalieri et al. |
| 2004/0077981 A1 | 4/2004 | Weaver, II et al. |
| 2008/0004557 A1* | 1/2008 | Wolanske .................. 602/19 |
| 2008/0234617 A1 | 9/2008 | Lee et al. |
| 2010/0121240 A1 | 5/2010 | Smith |
| 2010/0268140 A1 | 10/2010 | Berlese |
| 2011/0144551 A1 | 6/2011 | Johnson |
| 2011/0197362 A1 | 8/2011 | Chella et al. |
| 2011/0213284 A1 | 9/2011 | Garth et al. |

FOREIGN PATENT DOCUMENTS

| | | |
|---|---|---|
| WO | 0166051 | 9/2001 |
| WO | 03088877 | 10/2003 |
| WO | 2004093721 | 11/2004 |
| WO | 2005117769 | 12/2005 |
| WO | 2010098805 | 9/2010 |
| WO | 2011106764 | 9/2011 |

* cited by examiner (Inside)

(Outside)

(Outside)

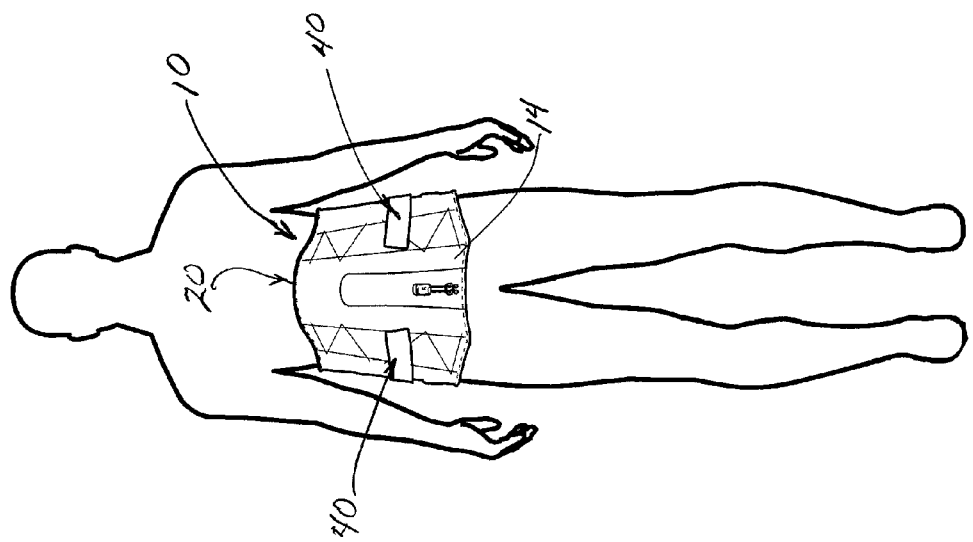
FIG. 8 (Back)
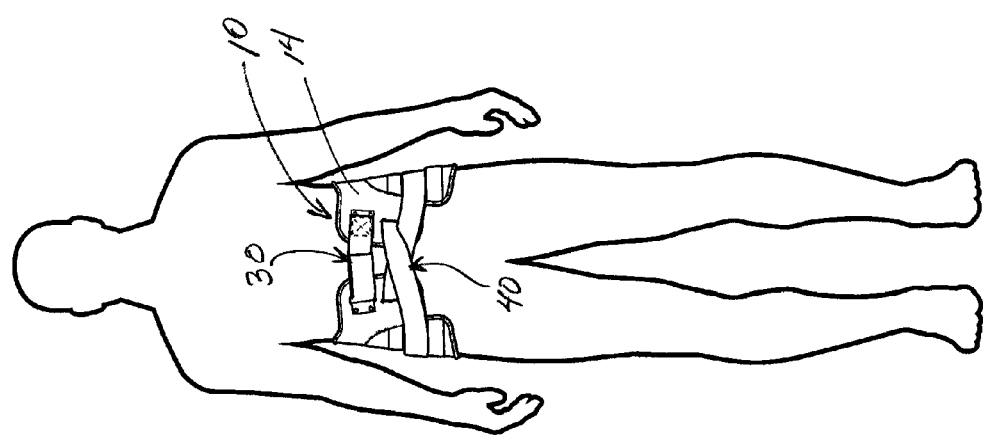
FIG. 7 (Front)

ADJUSTABLE LUMBO-SACRAL ORTHOSIS

CROSS-REFERENCE TO RELATED APPLICATIONS

This is a continuation-in-part application of U.S. patent application Ser. No. 13/472,882 filed May 16, 2012 which claims priority to U.S. Provisional Application No. 61/486,438, filed May 16, 2011 and U.S. Provisional Application No. 61/611,669, filed Mar. 16, 2012, and U.S. Provisional Application No. 61/622,204, filed Apr. 10, 2012.

BACKGROUND

There are various types of commercially available orthoses that are intended for stabilizing and immobilizing the lumbar and sacral region of the body for the treatment of low back pain due to lumbar sprain, spinal stenosis, disc herniation, and different degenerative spinal disorders. However, presently available lumbo-sacral orthosis suffer from one or more shortcomings or deficiencies.

No two human bodies are the same. Even among individuals with similar weight and body types, a lumbo-sacral orthosis that may serve one individual well, but may be ill fitting on another. Accordingly, there is a need for a lumbo-sacral orthosis that is easily adjustable to ensure a proper fit and to maintain substantial immobilization of the lumbar and sacral region of the wearer at all times, including while standing, sitting or walking.

Lumbo-sacral orthoses are typically prescribed by orthopedic doctors and fitted to patients by a fitting practitioner during an office visit to ensure a proper fit. However, if the patient removes the orthosis for bathing or other reasons, it is difficult for the patient to position and adjust the orthosis to achieve the same fit as when it was initially fitted by the fitting practitioner. Accordingly, there is a need for a lumbo-sacral orthosis which a wearer can replace after removal and achieve the same or substantially the same fit as when initially fitted by fitting practitioner.

Also, as a patient moves during the course of the day, commercially available lumbo-sacral orthosis tend to ride-up on the wearer when moving from standing position to a sitting position, particularly if the orthosis includes an abdominal panel. For example, when a wearer sits, the abdominal panel will often contact the wearer's lap causing the orthosis to be forced upwardly causing discomfort to the wearer. Additionally, when the wearer returns to a standing position, the orthosis may no longer be properly positioned and in full contact with the wearer's body. If the orthosis is not in full contact with the wearer's body, the wearer's lumbar and sacral region will not be properly supported or substantially immobilized, permitting the wearer to slouch causing further injury or delaying recovery. Accordingly, there is a need for an lumbo-sacral orthosis that will remain in place as the wearer moves throughout the day, remains comfortable and in full contact with the wearer's lumbar and sacral region and will permit the wearer to sit without causing the orthosis to be forced upwardly and out of proper position.

BRIEF DESCRIPTION OF THE DRAWINGS

FIG. 7 illustrates the lumbo-sacral orthosis of FIGS. 1 and 2 positioned on a wearer as viewed from the front.

FIG. 8 illustrates the lumbo-sacral orthosis of FIG. 7 positioned on a wearer as viewed from the back.

DESCRIPTION

Figure 1:
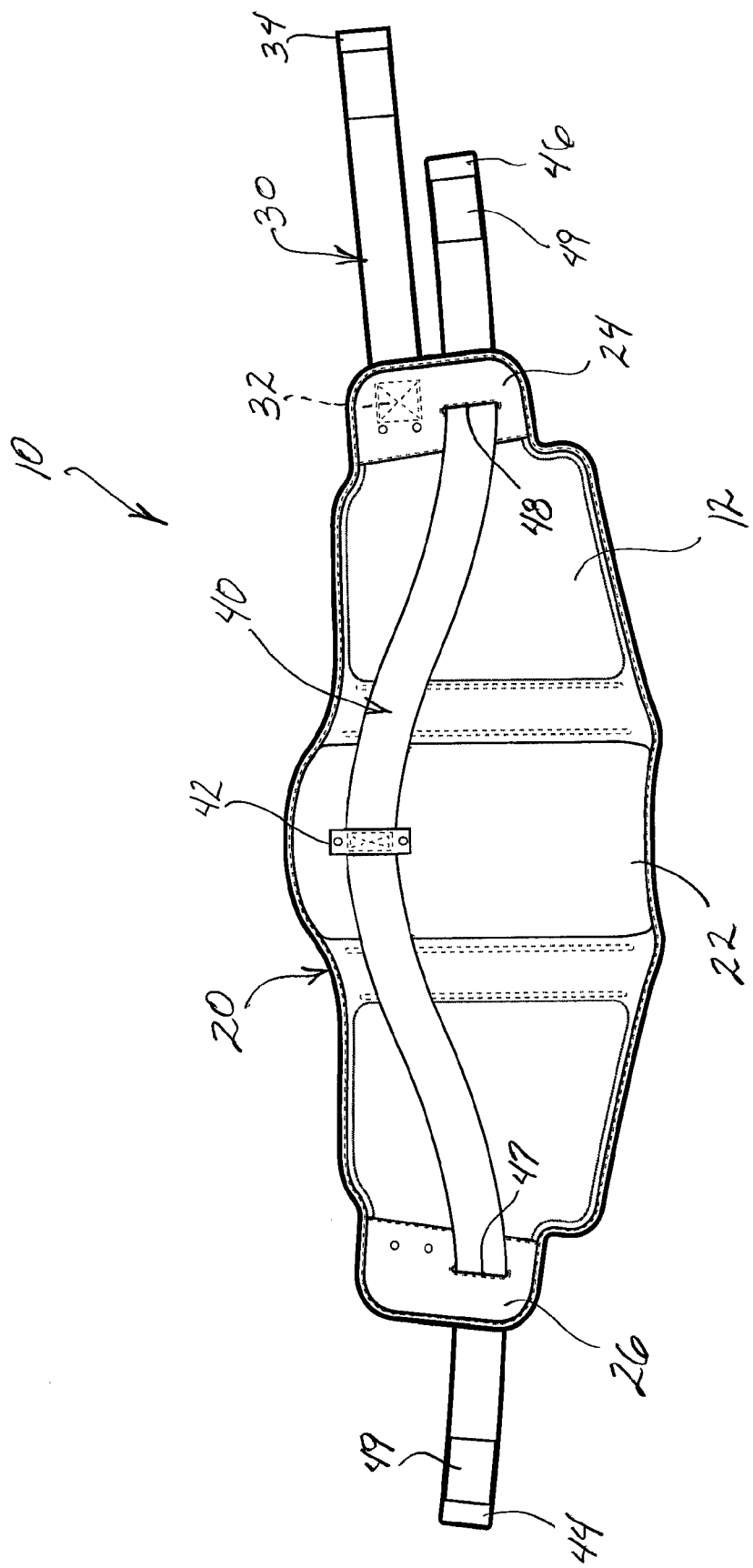
FIG. 1 illustrates one embodiment of a lumbo-sacral orthosis as viewed from the inside or body-contact side.
Figure 2:
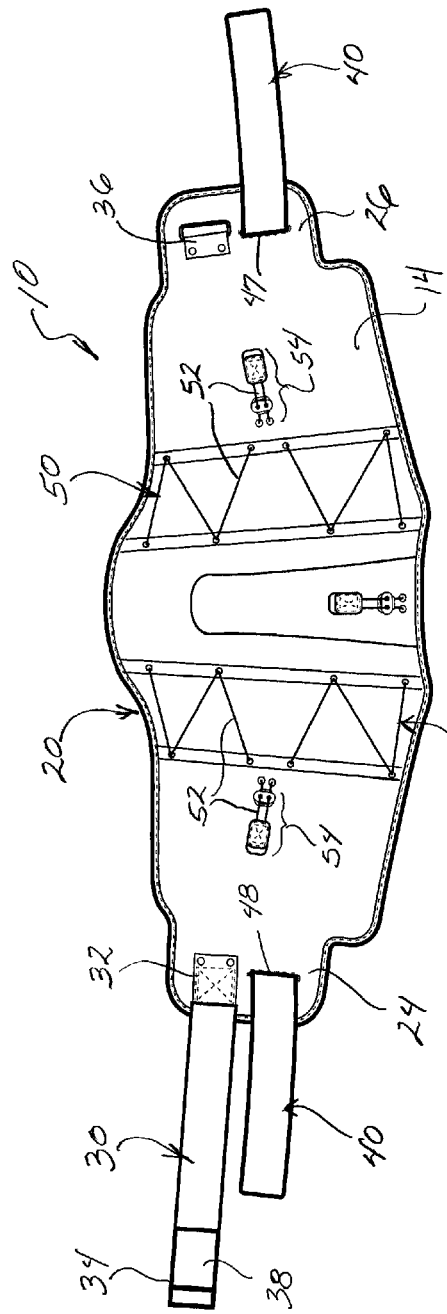
FIG. 2 illustrates one embodiment of a lumbo-sacral orthosis as viewed from the outside or exterior side.
Figure 3:
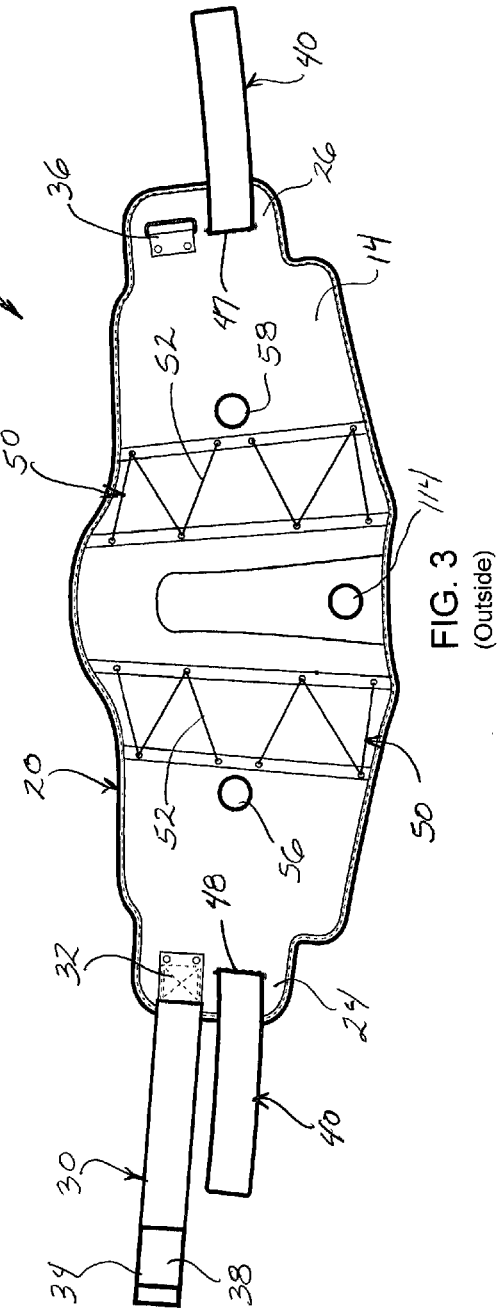
FIG. 3 illustrates another embodiment of a lumbo-sacral orthosis as viewed from the outside or exterior side.

Referring now to the drawing figures, wherein like reference numerals designate the same or corresponding parts throughout the several views, FIG. 1 illustrates one embodiment of a lumbo-sacral orthosis 10 as viewed from the inside face or body-contact side 12. FIG. 2 illustrates one embodiment of the lumbo-sacral orthosis 10 as viewed from the outside face or exterior side 14. FIG. 3 illustrates another embodiment of a lumbo-sacral orthosis 10 as viewed from the outside face 14.

The orthosis 10 has a main body 20, an exterior belt 30 and an interior belt 40. The main body has a middle section 22 and opposing ends 24, 26 and is sized to wrap around the body of a wearer at the wearer's lumbar and sacral region (see FIGS. 4-8). The inside face 12 and the outside face 14 of the main body are preferably made of wear-resistant, non-stretch fabric. As shown in FIG. 2, the exterior belt 30 has one end 32 secured to the outside 14 of the main body 20 (FIG. 2) proximate one end 24. The free end 34 of the exterior belt 30 may be inserted through a buckle 36 on the opposing end 26 on the outside of the main body 20. The free end 34 of the exterior belt 30 may include Velcro® patch 38 for attaching to a mating Velcro® patch or the fabric on the outside face of the main body 20. When being fitted with the orthosis, the wearer preferably pulls the free end 34 of the exterior strap 30 so the inside face 12 of the main body 20 is tight around his or her midsection. The free end 34 is then secured by Velcro to the outside face holding the orthosis in the proper position as illustrated in FIG. 5.

Figure 6:
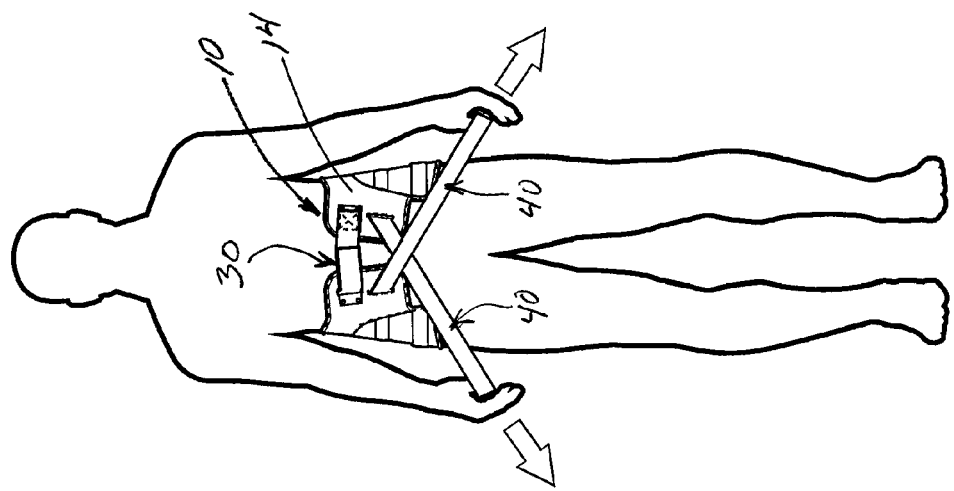
FIGS. 4-6 illustrate the steps for fitting lumbo-sacral orthosis of FIGS. 1 and 2 to a wearer.
Figure 5:
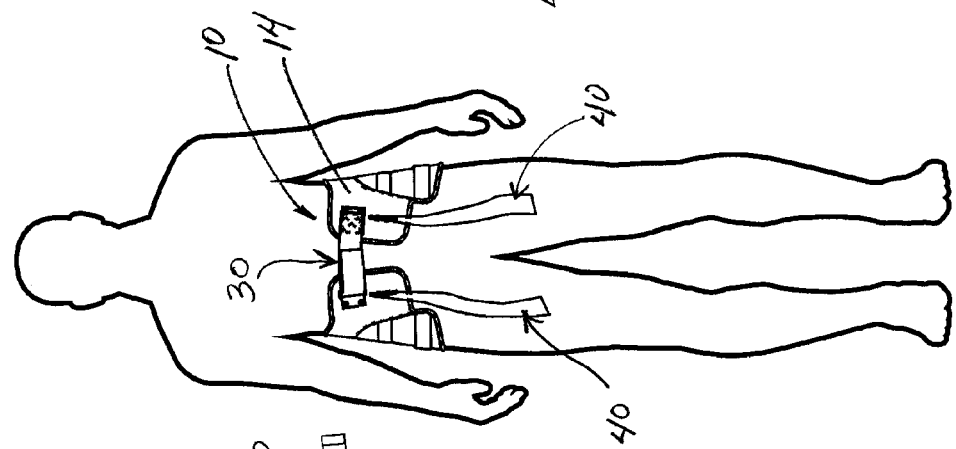
Figure 4:
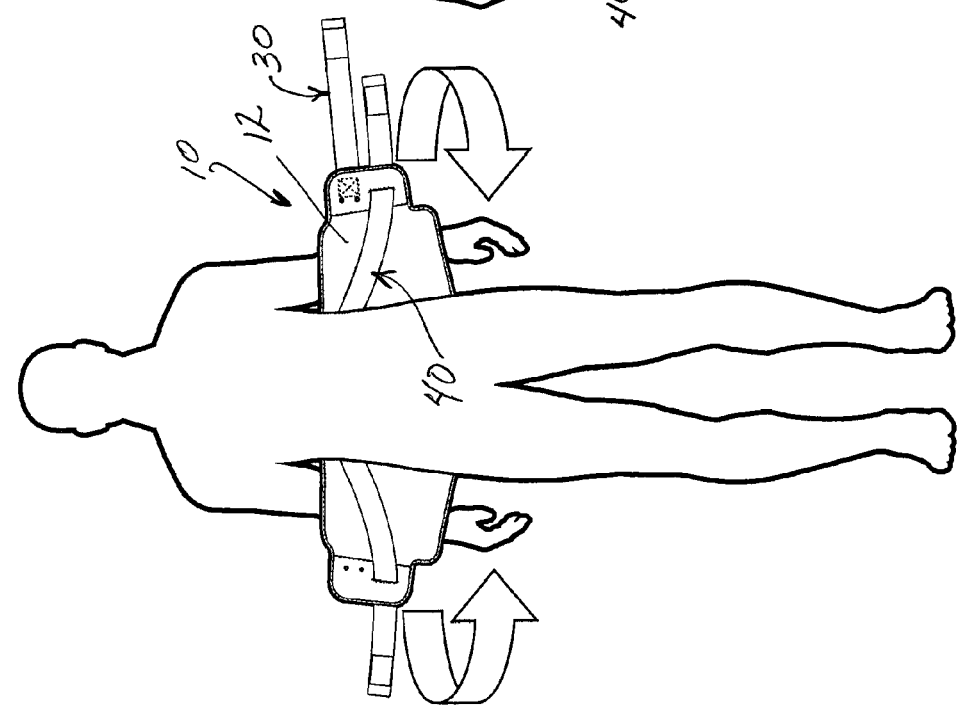

Referring to FIGS. 1, 5 and 6, the interior belt 40 is secured to the inside face 12 of the main body 20 proximate its middle by a loop 42 (FIG. 1). Each of the free ends 44, 46 pass through slots 47, 48 near the opposing ends 24, 26 of the main body 20 such that the free ends 44, 46 extend outside the main body 20. The free ends 44, 46 may also include Velcro® patches 49 (FIG. 1) for attaching to mating Velcro patches or the fabric on the outside face 14 of the main body 20. Comparing FIGS. 5-6, after the exterior belt 30 is tightened and secured, the wearer then grasps the free ends (FIG. 6), pulling outwardly to cinch the inner belt 40 tightly around the wearer's waist-groove. The free ends 44, 46 are then secured to the outside face 14 of the main body 20. It should be appreciated that by tightening the inner belt 40, it will cause inward circumferential compression around the wearer's body at the waist-groove. This circumferential compressive force tends to distract the spine and provides containment of the abdomen thereby aiding in the relief of back pain as the lumbar region is forced to stretch or extend. To further tighten the interior belt 40, a reel-based ratchet tightener such as available from Boa Technologies, Inc. and disclosed in U.S. Pat. No. 8,091, 182 (hereinafter a "Boa System"), may be incorporated and employed (not shown) to further pull and tighten the interior belt 40.

Referring again to FIGS. 2 and 3, lacing 50 may also be incorporated and employed to further tighten the main body 20 of the orthosis 10 around the midsection of the wearer. The lace cords 52 may be pulled and tightened by hand and then locked in place using a well known sliding lock mechanism 54 (see FIG. 2) or by incorporating and employing a Boa System as illustrated in FIG. 3, showing left and right reel-based ratchets 56, 58 of the Boa System.

Figure 9:
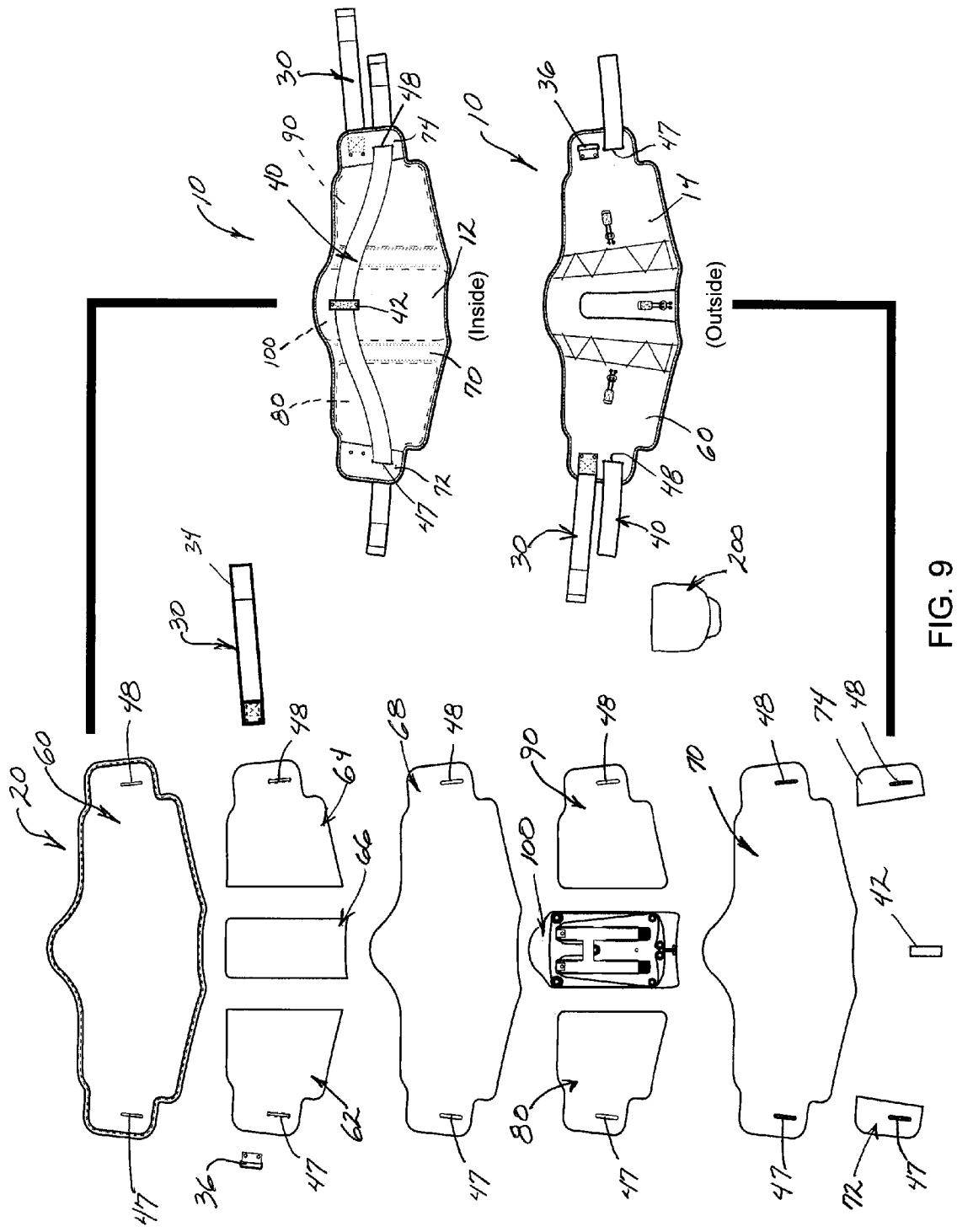
FIG. 9 is an exploded view of the lumbo-sacral orthosis of FIGS. 1 and 2.

FIG. 9 is an exploded view showing the various components of the orthosis of FIGS. 1 and 2. As shown, the orthosis 10 comprises several elements which are shown in stacked relation from the outside of the orthosis toward the inside of the orthosis. The outermost element is non-stretch fabric panel 60; then inner, fabric reinforcing panels 62, 64, 66; then a middle non-stretch fabric panel 68; then left and right side rigid panels 80, 90, and a rigid lumbar panel 100; then an interior stretch-fabric panel 70; and then interior end, fabric reinforcing panels 72, 74. The optional rigid abdominal panel 200 is positioned over the wearer's abdomen after the main body 20 of the othosis is in position around the wearer's waste with the outer belt is 30 loosely holding the orthosis in place. The outer belt 30 and inner belt 40 are then tightened and cinched as previously described.

Figure 10:
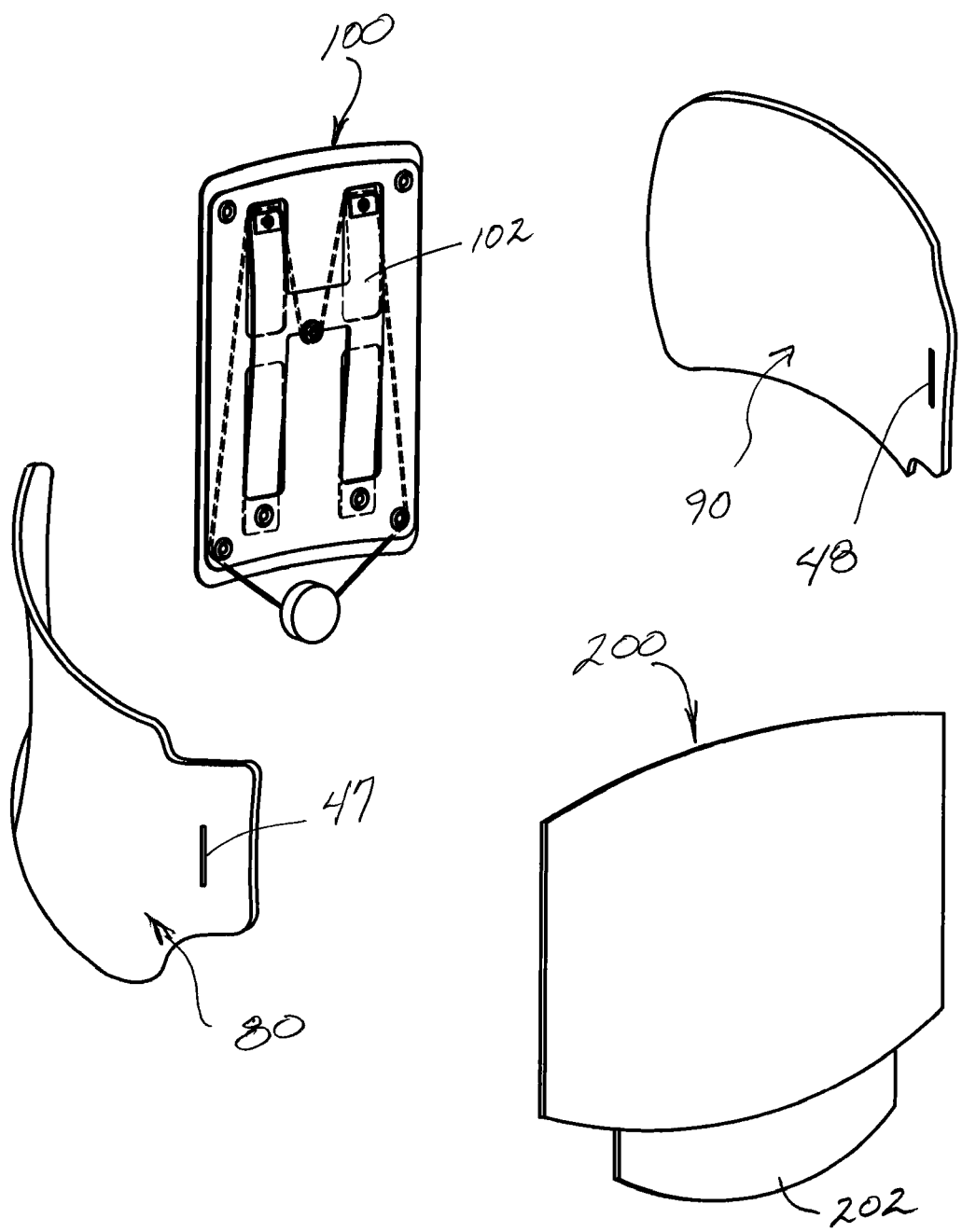
FIG. 10 is a perspective view illustrating one embodiment of the rigid panels of the lumbo-sacral orthosis of FIGS. 1-2 with the fabric and belts removed.

FIG. 10 is a perspective view showing the arrangement of the rigid panels with respect to one another within the orthosis 10 with the main body 20 and belts 30, 40 removed for clarity. As previously identified, the rigid panels include the left and right rigid side panels 80, 90 the rigid lumbar panel 100 and the rigid abdominal panel 200 with main body 20 and belts 30, 40 removed for clarity.

Referring to FIGS. 9 and 10, the left and right rigid side panels 80, 90 may be any desired configuration, but are preferably designed to be enclosed within the main body 20 of the orthosis 10. Slots 47, 48 are formed in the side panels to permit the free ends of the inner belt 40 to pass through the panels 80, 90 and extend to the outside of the main body 20. The rigid side panels 80, 90 are also preferably curved and contoured such that when the inner belt 40 is cinched tightly within the wearer's waist groove and the outer belt 30 is tightened, the side panels cooperate with the lumbar panel 100 and the optional abdominal panel 200 and the main body 20 of the orthosis 10 to substantially immobilize the lumbar and sacral regions of the wearer. Although the embodiment of FIG. 10 shows the rigid panels 80, 90 and 100 as being separate non-attached elements, if desired, the rigid side panels 80, 90 may be attached to the lumbar panel 100. For example, the panels 80, 90 and 100 may include ears that extend toward one another which may then be adjustably attached by mating Velcro® patches. Alternatively, the ears may be attached by removable pins or rivets extending through aligned holes in the mating ears. In yet another alternative embodiment, the side panels 80, 90 may be movably attached to the lumbar panel 100 by providing a groove or channel in the rearward end of the side panels 80, 90 which slidably receive outwardly extending tongues projecting from respective sides of the lumbar panel 100. In such an embodiment, as the outer belt 30 and inner belt 40 are tightened, the projecting tongues would slide inwardly within the groove or channel in the adjacent side panels 80, 90.

Figures 11, 12:
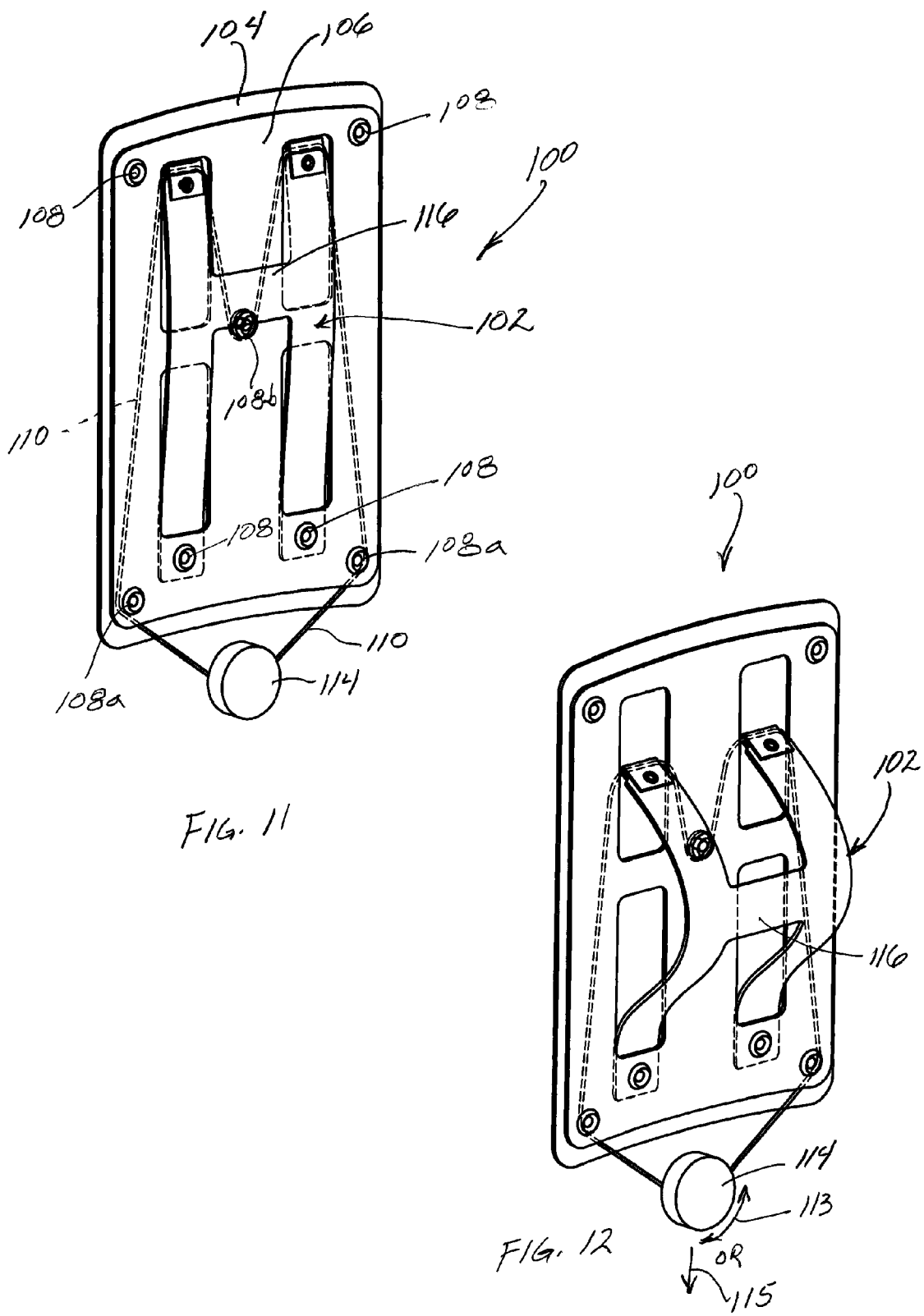
FIG. 11 is a perspective view illustrating an embodiment of an adjustable lumbar panel shown in the flat position.
FIG. 12 is a perspective view illustrating the adjustable lumbar panel of FIG. 11 in the flexed position.

FIGS. 11 and 12 illustrate an embodiment of the rigid lumbar panel 100 which includes a flexible element 102 that may be project inwardly as string or cord is pulled. The lumbar panel 100 includes a substantially planar but slightly curved or arched back wall 104 and a substantially planar but slightly curved or arched front wall 106. Rivets 108 or other suitable connectors connect the front wall 106 to the back wall 104 with spacers (not shown) disposed therebetween. The spacers are of sufficient height to permit a sting or cord 110 to pass between the front and back walls. One end of the flexible element 102 is also restrained between the front and back walls by rivets 108. The cord 110 passes around the lower spacers and rivets 108a as illustrated, extends through loops 112 at the upper end of the flexible element 102 and around the centrally positioned spacer and rivet 108b. The ends of the cord may be received in a real-ratchet 114 of a Boa System (see embodiment of FIG. 3). Alternatively, or the ends of the cord may be received by a sliding lock mechanism (see embodiment of FIG. 2).

In use, a wearer would rotate the reel-ratchet 114 of the Boa System as indicated by arrow 113 in FIG. 12 or pull downwardly on the cord as indicated by arrow 115 causing the flexible element to bow inwardly toward the wearers lumbar region as illustrated in FIG. 12. This independently movable flexible element 102 allows the wearer to adjust the lumbar panel to ensure and maintain full contact with the wearers body to further immobilize the lumbar and sacral region of the wearer. Although FIG. 12 shows the flexible element as being joined by a horizontal bar 116 such that the left and right sides of the flexible element move together, it may be desired to eliminate the horizontal bar 116 to permit the left and right sides of the flexible member 10 to bow out independently of each other. It should also be appreciated that separate cords may be provided such that the wearer may pull each cord to independently adjust the right and left sides of the flexible member. Likewise the flexible element 102 may be rotated 90 degrees such that the flexible members bows inwardly in a horizontal direction rather than vertically. In such an embodiment, the wearer would pull on the chords in a horizontal direction from the right and/or left sides. Alternatively, the flexible element may be rotated 180 degrees such that the wearer would pull upwardly (as opposed to downwardly as alternatively shown in FIG. 12). Of course if a Boa System is utilized, the reel-ratchet could be placed anywhere on the orthosis for easy reach by the wearer and the orientation of the flexible element could be vertical or horizontal.

Figure 13:
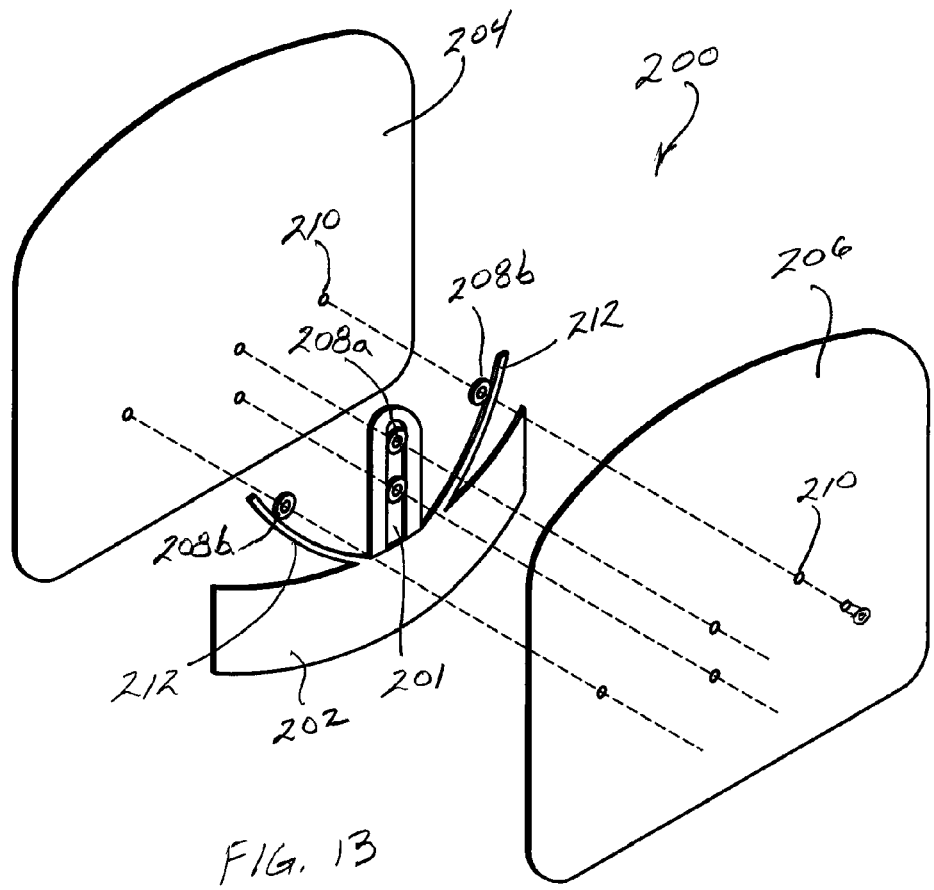
FIG. 13 is a perspective view of one embodiment of an abdominal panel.

FIG. 13 illustrates an embodiment of an abdominal panel 200 which includes an independently movable lower element 202 that will retract vertically when the wearer of the orthosis 10 moves between standing and sitting positions as the lower element comes in contact with the wearers lap when he or she sits, but will return to the extended position when standing. In the embodiment of FIG. 13, the abdominal panel 200 includes a back wall 204 and a front wall 206. Rivets 108 or other suitable connectors connect the front wall 206 to the back wall 204 with spacers 208 disposed therebetween through aligned holes 210. The spacers 208 are of sufficient height to permit the lower element 202 to move vertically between the front and back walls. Centrally located spacers 208a are received within a vertical channel 201 of the movable lower element 202 to serve as guides such that the lower element will move substantially vertically between the front and back walls. Outer spacers 208b are positioned to engage upwardly extending resilient biasing arms 212 which serve to biasing the movable lower element 202 in the extended position.

Figure 14:
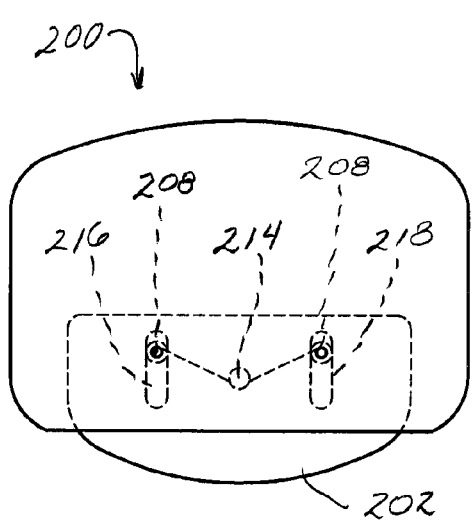
FIG. 14 is a front elevation view of another embodiment of an abdominal panel.

FIG. 14 is an alternative embodiment of the abdominal panel 200. Rather than utilizing biasing arms 212 as in the previous embodiment, a torsion spring 214 is utilized to bias the lower element 202 downwardly. In this embodiment the lower element includes two channels 216, 218 which receive spacers 208 to vertically guide the lower element 202.

Figure 15:
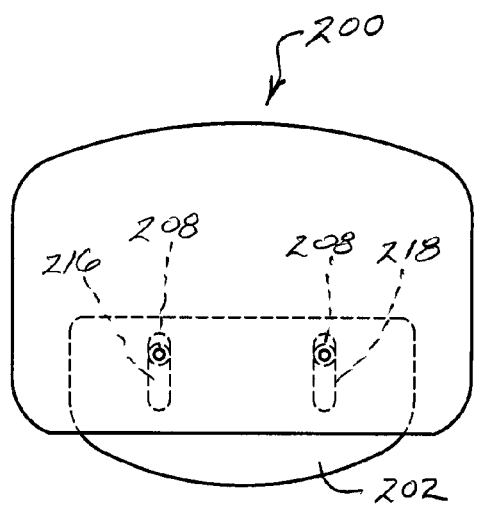
FIG. 15 is a front elevation view of another embodiment of an abdominal panel.

FIG. 15 is yet another alternative embodiment of the abdominal panel 200 which is substantially identical to the embodiment of FIG. 14, but without the torsion spring or any other biasing element.

The foregoing description is presented to enable one of ordinary skill in the art to make and use the invention and is provided in the context of a patent application and its requirements. Various modifications to the preferred embodiment of the apparatus, and the general principles and features of the system and methods described herein will be readily apparent to those of skill in the art. Thus, the present invention is not to be limited to the embodiments of the apparatus, system and methods described above and illustrated in the drawing figures, but is to be accorded the widest scope consistent with the spirit and scope of the appended claims.

The invention claimed is:

1. A lumbo-sacral orthosis, comprising:
(a) a main body member having an inside face, an outside face, a middle section, and first and second ends, said main body member sized so as to be capable of wrapping substantially around a body of a wearer at the wearer's lumbar and sacral region;
(b) an outer belt having a length and a first end, the first end attached to said first side of said main body member, said length cooperable with said second end of said main body member so as to hold said main body member at the wearer's lumbar and sacral region with said inside face of said main body member adjacent the wearer's body;
(c) an inner belt having a length disposed interiorly adjacent said inside face of said middle section of said main body member, said inner belt capable of being cinched independently of said main body member such that when cinched, said interior length of said inner belt is in contact with said wearer's lumbar region and said waist groove causing compression substantially around said wearer's body at said wearer's lumbar region and waist groove and wherein said inner belt includes: a first end passing through said main body member proximate said first end of said main body member and extending exteriorly from said outside face; and a second end passing through said main body member proximate said second end of said main body member and extending exteriorly from said outside face.

2. The lumbo-sacral orthosis of claim 1, further comprising:
a rigid lumbar panel disposed between said inside face and said outside face of said main body member at said middle section.

3. The lumbo-sacral orthosis of claim 2, further comprising:
a first rigid side panel disposed between said inside face and said outside face of said main body member and between said middle section and said first end of said main body member; and
a second rigid side panel disposed between said inside face and said outside face of said main body member and between said middle section and said second end of said main body member.

4. A lumbo-sacral orthosis, comprising:
(a) a main body member having an inside face, an outside face, a middle section, and first and second ends, said main body member sized so as to be capable of wrapping substantially around a body of a wearer at the wearer's lumbar and sacral region;
(b) an outer belt having a length and a first end, the first end attached to said first side of said main body member, said length cooperable with said second end of said main body member so as to hold said main body member at the wearer's lumbar and sacral region with said inside face of said main body member adjacent the wearer's body;
(c) an inner belt having a length disposed interiorly adjacent said inside face of said middle section of said main body member, said inner belt capable of being cinched independently of said main body member such that when cinched, said interior length of said inner belt is in contact with said wearer's lumbar region and said waist groove causing compression substantially around said wearer's body at said wearer's lumbar region and waist groove; and
(d) a rigid lumbar panel disposed between said inside face and said outside face of said main body member at said middle section, wherein said rigid lumbar panel includes a rigid wall and a flexible element movable independently of said rigid wall between a flat position and an inward bowed position.

5. The lumbo-sacral orthosis of claim 4, further comprising:
a first rigid side panel disposed between said inside face and said outside face of said main body member and between said middle section and said first end of said main body member; and
a second rigid side panel disposed between said inside face and said outside face of said main body member and between said middle section and said second end of said main body member.

6. The lumbo sacral orthosis of claim 4 further including a cord which when pulled, causes said flexible element to move from said flat position to said inward bowed position.

7. The lumbo sacral orthosis of claim 6 further including a rotatable reel-based ratchet which when rotated pulls said cord to cause said flexible element to move from said flat position to said inward bowed position.

8. A lumbo-sacral orthosis, comprising:
(a) a main body member having an inside face, an outside face, a middle section, and first and second ends, said main body member sized so as to be capable of wrapping substantially around a body of a wearer at the wearer's lumbar and sacral region;
(b) an outer belt having a length and a first end, the first end attached to said first side of said main body member, said length cooperable with said second end of said main body member so as to hold said main body member at the wearer's lumbar and sacral region with said inside face of said main body member adjacent the wearer's body;
(c) an inner belt having a length disposed interiorly adjacent said inside face of said middle section of said main body member, said inner belt capable of being cinched independently of said main body member such that when cinched, said interior length of said inner belt is in contact with said wearer's lumbar region and said waist groove causing compression substantially around said wearer's body at said wearer's lumbar region and waist groove and (d) a rigid abdominal panel, said rigid abdominal panel disposed adjacent the wearer's abdomen interiorly of said inside face of said main body member when said main body member is wrapped around the body of the wearer, wherein said rigid abdominal panel, includes a rigid wall and a lower element vertically movable independently of said rigid wall between an extended position and a retracted position.

9. The lumbo-sacral orthosis of claim 8 wherein said lower element is biased in a direction toward said extended position.

10. A method of supporting and substantially immobilizing the lumbar and sacral regions of an individual, comprising:
   (a) wrapping a main body member substantially around the individual's body individual's lumbar and sacral region, said main body member having an inside face, an outside face, a middle section, and first and second ends;
   (b) employing an outer belt to hold said main body member at the individual's lumbar and sacral region with said inside face of said main body member adjacent the individual's body;
   (c) cinching an inner belt to compress the individual's body at the individual's waist groove, said inner belt having a length disposed interiorly adjacent said inside face of said middle section of said main body member, whereby, when cinched, said interior length of said inner belt is in contact with said wearer's lumbar region and waist groove causing compression substantially around said wearer's body at said wearer's lumbar region and waist groove, wherein said inner belt includes, a first end passing through said main body member proximate said first end of said main body member and extending exteriorly from said outside face; and a second end passing through said main body member proximate said second end of said main body member and extending exteriorly from said outside face.

11. The method of claim 10 wherein said main body member supports a rigid lumbar panel disposed between said inside face and said outside face of said main body member at said middle section.

12. The method of claim 11 wherein said main body member further supports a first rigid side panel disposed between said inside face and said outside face of said main body member and between said middle section and said first end of said main body member, and a second rigid side panel disposed between said inside face and said outside face of said main body member and between said middle section and said second end of said main body member.

13. A method of supporting and substantially immobilizing the lumbar and sacral regions of an individual, comprising:
   (a) wrapping a main body member substantially around the individual's body individual's lumbar and sacral region, said main body member having an inside face, an outside face, a middle section, and first and second ends;
   (b) employing an outer belt to hold said main body member at the individual's lumbar and sacral region with said inside face of said main body member adjacent the individual's body;
   (c) cinching an inner belt to compress the individual's body at the individual's waist groove, said inner belt having a length disposed interiorly adjacent said inside face of said middle section of said main body member, whereby, when cinched, said interior length of said inner belt is in contact with said wearer's lumbar region and waist groove causing compression substantially around said wearer's body at said wearer's lumbar region and waist groove,
   wherein said main body member supports a rigid lumbar panel disposed between said inside face and said outside face of said main body member at said middle section and wherein said rigid lumbar panel includes a rigid wall and a flexible element movable independently of said rigid wall between a flat position and an inward bowed position.

14. The method of claim 13 wherein said inner belt includes, a first end passing through said main body member proximate said first end of said main body member and extending exteriorly from said outside face; and a second end passing through said main body member proximate said second end of said main body member and extending exteriorly from said outside face.

15. The method of claim 13 wherein said main body member further supports a first rigid side panel disposed between said inside face and said outside face of said main body member and between said middle section and said first end of said main body member, and a second rigid side panel disposed between said inside face and said outside face of said main body member and between said middle section and said second end of said main body member.

16. The method of claim of claim 13 further comprising:
   pulling a cord to cause said flexible element to move from said flat position to said inward bowed position.

17. The method of claim of claim 16 wherein the step of pulling said cord includes rotating rotatable reel-based ratchet to cause said flexible element to move from said flat position to said inward bowed position.

18. A method of supporting and substantially immobilizing the lumbar and sacral regions of an individual, comprising:
   (a) wrapping a main body member substantially around the individual's body individual's lumbar and sacral region, said main body member having an inside face, an outside face, a middle section, and first and second ends;
   (b) employing an outer belt to hold said main body member at the individual's lumbar and sacral region with said inside face of said main body member adjacent the individual's body;
   (c) cinching an inner belt to compress the individual's body at the individual's waist groove, said inner belt having a length disposed interiorly adjacent said inside face of said middle section of said main body member, whereby, when cinched, said interior length of said inner belt is in contact with said wearer's lumbar region and waist groove causing compression substantially around said wearer's body at said wearer's lumbar region and waist groove,
   wherein said main body member further supports a rigid abdominal panel disposed adjacent the wearer's abdomen interiorly of said inside face of said main body member wherein said rigid abdominal panel, includes a rigid wall and a lower element vertically movable independently of said rigid wall between an extended position and a retracted position.

19. The method of claim of claim 18 wherein said lower element is biased in a direction toward said extended position.

* * * * *